United States Patent
Wuerstlein et al.

(10) Patent No.: US 9,995,601 B2
(45) Date of Patent: Jun. 12, 2018

(54) CAPACITIVE PROXIMITY SENSOR FOR A MOTOR VEHICLE, COLLISION PROTECTION DEVICE FOR A MOTOR VEHICLE AND MOTOR VEHICLE WITH A CAPACITIVE PROXIMITY SENSOR

(71) Applicant: BROSE FAHRZEUGTEILE GMBH & CO. KOMMANDITGESELLSCHAFT, HALLSTADT, Hallstadt (DE)

(72) Inventors: Holger Wuerstlein, Zeil am Main (DE); Florian Pohl, Ebersdorf (DE)

(73) Assignee: BROSE Fahrzeugteile GmbH & Co. Kommanditgesellschaft, Hallstadt, Hallstadt (DE)

( * ) Notice: Subject to any disclaimer, the term of this patent is extended or adjusted under 35 U.S.C. 154(b) by 110 days.

(21) Appl. No.: 15/047,911

(22) Filed: Feb. 19, 2016

(65) Prior Publication Data
US 2016/0245671 A1  Aug. 25, 2016

(30) Foreign Application Priority Data

Feb. 19, 2015 (DE) .......... 10 2015 002 128

(51) Int. Cl.
| | | |
|---|---|---|
| G01R 27/26 | (2006.01) |
| G01D 5/24 | (2006.01) |
| G01N 27/22 | (2006.01) |
| B60R 21/0134 | (2006.01) |
| G01V 3/02 | (2006.01) |

(52) U.S. Cl.
CPC ......... *G01D 5/2405* (2013.01); *G01N 27/221* (2013.01); *G01R 27/2605* (2013.01); *B60R 21/0134* (2013.01); *G01V 3/02* (2013.01)

(58) Field of Classification Search
CPC .... G01R 27/2605; G01N 27/221; G01D 5/24; H03K 17/955; H03K 2217/96078; H03K 2217/9607
USPC .................................... 324/663, 658
See application file for complete search history.

(56) References Cited

U.S. PATENT DOCUMENTS

| | | | |
|---|---|---|---|
| 8,344,739 B2 | 1/2013 | Van Gastel et al. | |
| 9,442,145 B2* | 9/2016 | Pohl | ............ G01R 27/2605 |
| 2002/0154039 A1* | 10/2002 | Lambert | ............ H03K 17/955 |
| | | | 341/33 |
| 2008/0122456 A1 | 5/2008 | Moon et al. | |
| 2010/0060489 A1 | 3/2010 | Fasshauer | |

(Continued)

FOREIGN PATENT DOCUMENTS

| | | |
|---|---|---|
| CN | 1839326 A | 9/2006 |
| CN | 101636908 A | 1/2010 |
| CN | 101943586 A | 1/2011 |

(Continued)

*Primary Examiner* — Amy He
(74) *Attorney, Agent, or Firm* — Laurence A. Greenberg; Werner H. Stemer; Ralph E. Locher

(57) ABSTRACT

A capacitive proximity sensor for a motor vehicle contains a transmission electrode for producing a measurement field and a reception electrode for detecting at least part of the measurement field. Furthermore, the proximity sensor contains a screen electrode that is disposed to form the measurement field between the transmission electrode and the reception electrode. The proximity sensor is in particular provided for use in a collision protection device for the motor vehicle.

4 Claims, 3 Drawing Sheets

(56) References Cited

U.S. PATENT DOCUMENTS

| | | | | |
|---|---|---|---|---|
| 2014/0239981 A1* | 8/2014 | Zibold | ................. | G01V 3/088 |
| | | | | 324/680 |
| 2015/0048845 A1* | 2/2015 | Petereit | ............... | H03K 17/955 |
| | | | | 324/663 |

FOREIGN PATENT DOCUMENTS

| DE | 102009059202 A1 | 2/2011 |
|---|---|---|
| DE | 102011053897 A1 | 3/2013 |
| EP | 1712418 A2 | 10/2006 |

* cited by examiner

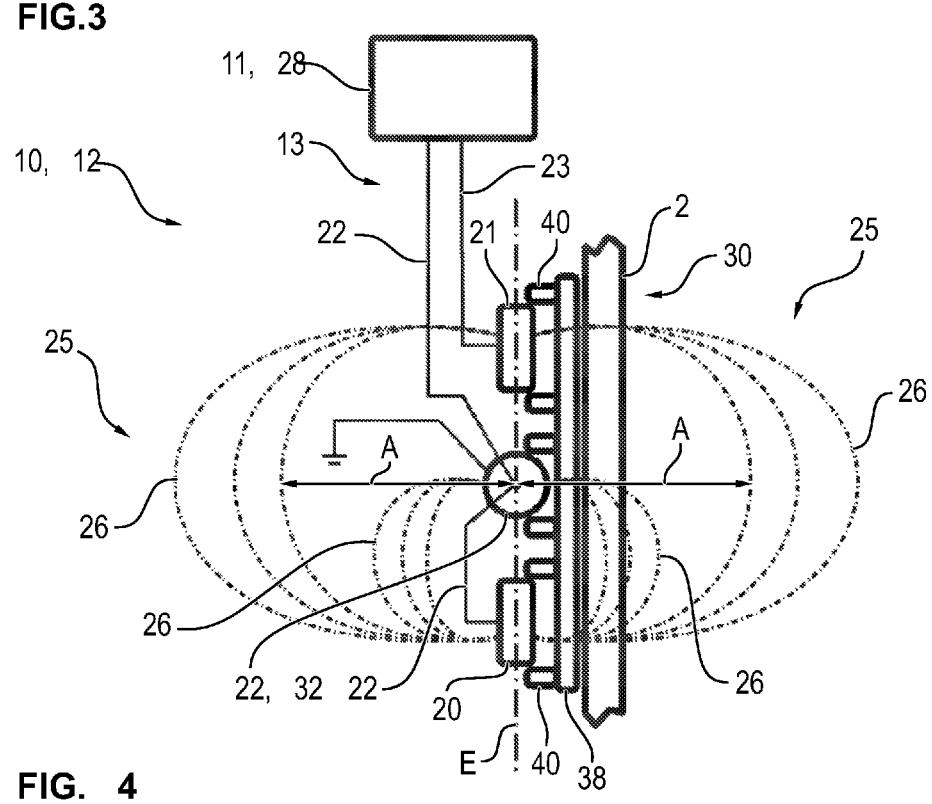
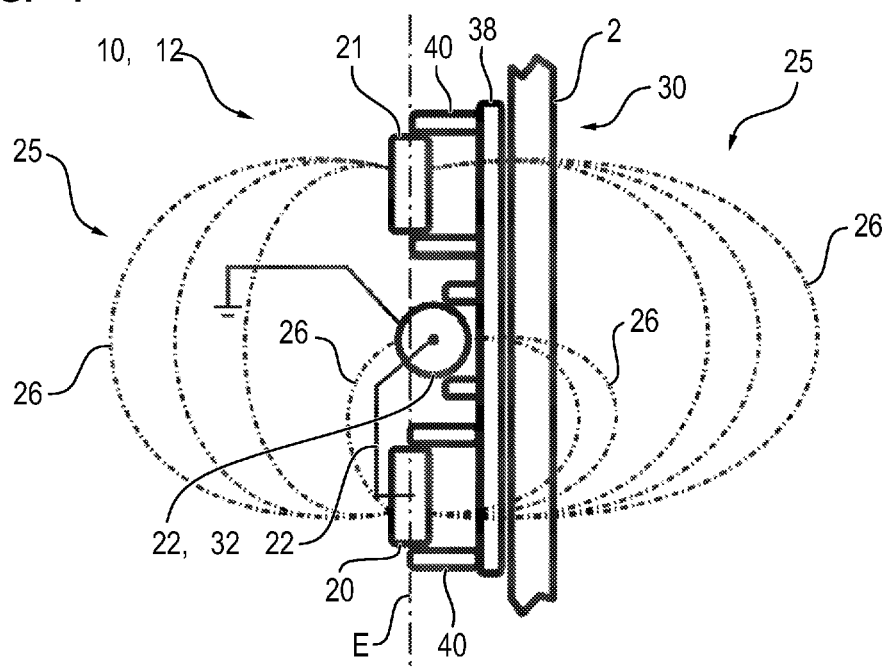

CAPACITIVE PROXIMITY SENSOR FOR A MOTOR VEHICLE, COLLISION PROTECTION DEVICE FOR A MOTOR VEHICLE AND MOTOR VEHICLE WITH A CAPACITIVE PROXIMITY SENSOR

CROSS-REFERENCE TO RELATED APPLICATION

This application claims the priority, under 35 U.S.C. § 119, of German application DE 10 2015 002 128.1, filed Feb. 19, 2015; the prior application is herewith incorporated by reference in its entirety.

BACKGROUND OF THE INVENTION

Field of the Invention

The invention concerns a capacitive proximity sensor for a motor vehicle that is in particular configured to detect the approach of an object by two mutually separate sensor electrodes. Furthermore, the invention concerns a collision protection device for a motor vehicle with such a proximity sensor. Moreover, the invention concerns a motor vehicle with such a proximity sensor.

Capacitive proximity sensors are often used in modern motor vehicles, in particular in automobiles, in order for example to monitor the displacement of vehicle parts that are driven by electric motors in a collision protection device. Using the capacitive sensors, in this case the region of control travel disposed in front of the vehicle part is monitored for the presence of an obstacle. Such a capacitive sensor is preferably operated according to the so-called transmitter-receiver principle. In this case, a measurement signal in the form of an electrical alternating field is output by a first sensor electrode (hereinafter referred to as a transmission electrode), the measurement signal being in turn received by a second sensor electrode (hereinafter referred to as a reception electrode). The transmission electrode and the reception electrode thus form a sensor capacitor with a sensor capacitance that can be determined using the measurement signal. An obstacle within the electrical alternating field causes an abnormal change of the detected sensor capacitance, resulting in a control unit associated with the collision protection device stopping the displacement of the vehicle part and possibly reversing the displacement (i.e. reversing the displacement direction).

In an alternative implementation, capacitive proximity sensors are also used in motor vehicles to contactlessly detect an intention to open a door on the part of a vehicle user. In this case the capacitive proximity sensors are mostly (also configured according to the transmitter-receiver principle) configured to contactlessly detect a vehicle proximity event, in particular an approach to the respective proximity sensor. The measurement signal determined in doing so is then compared with a stored reference signal within a door opening device. In the event of sufficient agreement of the measurement signal with the reference signal, the intention to open a door on the part of the vehicle user is concluded and, possibly following a check on the access authorization of the vehicle user, the displacement of the respective vehicle door, mostly the tailgate, is triggered.

In both cases the capacitive proximity sensors are mostly disposed on the motor vehicle at a short distance from the outer skin of the vehicle. In the context of the collision protection device, the sensors are frequently disposed on a vehicle door, in particular the tailgate, hidden behind internal door cladding. During normal use of the motor vehicle, it frequently happens that moisture, such as for example rain water, is precipitated onto the outer skin of the vehicle and in the process is also disposed in the region of the electrical alternating field of the capacitive proximity sensor. The moisture can in this case influence the electrical alternating field, which is falsely interpreted by the analysis unit associated with the sensor as the approach of a person towards the sensor (in particular since the human body also consists to a large extent of water) and thus results in the incorrect triggering of the respective function (stopping the current displacement or outputting a door opening command).

SUMMARY OF THE INVENTION

The object of the invention is to enable highly failsafe operation of a capacitive proximity sensor at the same time as a simple design.

The capacitive (proximity) sensor according to the invention for a motor vehicle contains a sensor electrode referred to as a transmission electrode for producing a measurement field and a further sensor electrode referred to as a reception electrode for detecting at least part of the measurement field. Furthermore, the capacitive sensor contains a screen electrode that is (spatially) disposed between the transmission electrode and the reception electrode and that is configured and provided for (targeted) formation of the measurement field (formed between the transmission electrode and the reception electrode).

"Disposed spatially between the transmission electrode and the reception electrode" means here and below in particular that the screen electrode is disposed exactly on a sensor plane spanned by the transmission and reception electrodes (and bounded by the same on two sides) or at least at a short distance from the sensor plane in relation to the width (or thickness) of the screen electrode (for example up to twice the width or thickness). In this case the screen electrode is also disposed at a shorter distance from the transmission electrode than the reception electrode.

Because the screen electrode is disposed between the transmission and reception electrodes, it is advantageously achieved that part of the measurement field produced by the transmission electrode is already absorbed by the screen electrode and is thus not sensed by the reception electrode. In other words, field lines of the measurement field, which in the absence of the screen electrode would run at a short distance from the sensor plane (i.e. field lines with an extended and slightly curved course), do not run starting from the transmission electrode as far as the reception electrode, but already end at the screen electrode. As a result, the sensitivity of the sensor is reduced in a region lying directly between the transmission and reception electrodes. In a simplified (pictorial) representation, an approximately lens-shaped region of the measurement field (parallel to the sensor plane when seen in the viewing direction) is "hidden". As a result, in particular for the case in which the capacitive sensor is disposed at a short distance from an outer surface of the vehicle, the sensitivity of the sensor in the region of the outer surface can be reduced in a simple manner and hence the robustness against false triggering because of liquid or dirt on the surface of the vehicle can be increased. In particular, it is enabled that moisture adhering to the outer surface of the vehicle has no or only a negligibly small influence on the measurement field detected by means of the reception electrode (in particular on the part of the measurement field not absorbed by the screen electrode).

In a preferred implementation, the screen electrode is in particular fixedly (i.e. unchangeably) connected to reference potential, preferably ground potential.

In a particularly preferred implementation of the invention, the transmission electrode and/or the reception electrode is/are connected by a shielded connecting line to an analysis unit that is associated with the sensor. The shielded connecting line is for example a coaxial cable or a flat cable that is enclosed by a shielding conductor. Advantageously, in this case the screen electrode (disposed between the transmission and reception electrodes) is formed by the cable shield of the shielded connecting line. In this case, the shielded connecting line is led from an end of the transmission electrode (or the reception electrode) that is remote from the analysis unit, between the transmission and reception electrodes (for example parallel to both) to the analysis unit. This enables a particularly simple design of the sensor, in particular as the cable shield of the shielded connecting line is connected to reference potential anyway and thus additional (ground) connections and material costs for a separate screen electrode are dispensed with.

Within the scope of the invention, it is in principle also conceivable that—in particular depending on the intended form of the measurement field and sensitivity of the sensor—a shielded connecting cable is fed back between both sensor electrodes both from the transmission electrode and from the reception electrode, so that there are two screen electrodes.

In a preferred implementation, the transmission electrode and the reception electrode are each implemented as elongated sensor electrodes (for example as flat conductors and/or round conductors). "Elongated" thus means here and below that the length of the respective sensor electrodes is several times greater than the width thereof (or in the case of round conductors than the diameter thereof).

In a further advantageous implementation, the capacitive sensor contains a base support, on which the transmission electrode, the reception electrode and the screen electrode are mounted, in particular by mounting elements that are disposed on the base support. The holding elements are in this case joined to the base support, preferably in one piece, at predetermined positions, so that the electrodes are each held at a fixed predetermined distance from each other. A mounting assembly is thus formed by the base support and the electrodes mounted thereon, which is configured and provided to be fixed on the motor vehicle as an independent (premounted) assembly. As an alternative to the holding elements, other types of fixing for the transmission electrode, the reception electrode and the screen electrode to the base support are also conceivable within the scope of the invention, such as for example adhesive bonds, (ultrasonic) welded joints, riveted joints or similar.

The capacitive sensor is preferably configured and provided to be fixed at a short distance from the outer surface of the motor vehicle—for example as a sensor for detecting an intention to open a door, on the inside of a (rear) bumper or as a collision protection sensor on the inside of a vehicle door (in particular the tailgate) hidden under inner door cladding.

The collision protection device according to the invention for the motor vehicle contains the capacitive sensor described above and a control unit. The control unit is configured to form a conclusion regarding the presence of an object within a region monitored by the measurement field using the part of the measurement field detected by the reception electrode. In this case the analysis unit of the sensor is preferably integrated within the control unit. The monitored region is preferably both the region of control travel upstream of the respective vehicle part in the opening direction (i.e. outside the vehicle) and also the upstream region of control travel in the closing direction (within the vehicle). In other words, the collision protection is configured to monitor the adjustment movement when opening the vehicle part (for example the tailgate) such that the vehicle part does not strike an object disposed in the surroundings of the vehicle (for example a bystander), and to monitor the closing movement when closing the vehicle part in the manner of a trapping prevention device such that no object is trapped between the vehicle part and the fixed vehicle body. In particular, in the latter case it can occur that rain water running on the exterior of the vehicle can also be incorrectly interpreted as the presence of an object between the vehicle part and the fixed vehicle body, and thus a (further) closing movement of the vehicle part is prevented.

The control unit can be in the form of a non-programmable electronic circuit within the scope of the invention, and can be integrated for example within a controller of a servomotor driving the vehicle part. However, the control unit is preferably formed by a microcontroller, in which the functionality for performing the collision protection method is implemented in the form of a software module. The software module can in particular form a component of overarching control software (firmware) of the controller of the servomotor here. The same also applies to the analysis unit of the sensor, which is implemented in particular as part of the control unit.

A contactless access system for the motor vehicle is also considered to be innovative, and contains the capacitive sensor described above as well as a control unit that is configured to contactlessly detect an intention to open a door on the part of a vehicle user using the part of the measurement field that is detected by the reception electrode and possibly to output a door opening signal to the servomotor driving the vehicle door.

The motor vehicle according to the invention contains the sensor described above. The sensor is used here in an advantageous implementation in the collision protection device described above. In addition or alternatively, the sensor is (also) used in this case in the access system described above.

Other features which are considered as characteristic for the invention are set forth in the appended claims.

Although the invention is illustrated and described herein as embodied in a capacitive proximity sensor for a motor vehicle, a collision protection device for a motor vehicle and a motor vehicle with a capacitive proximity sensor, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIGS. 3 and 4 are illustrations each showing an exemplary embodiment of the proximity sensor.

DETAILED DESCRIPTION OF THE INVENTION

Figure 1:
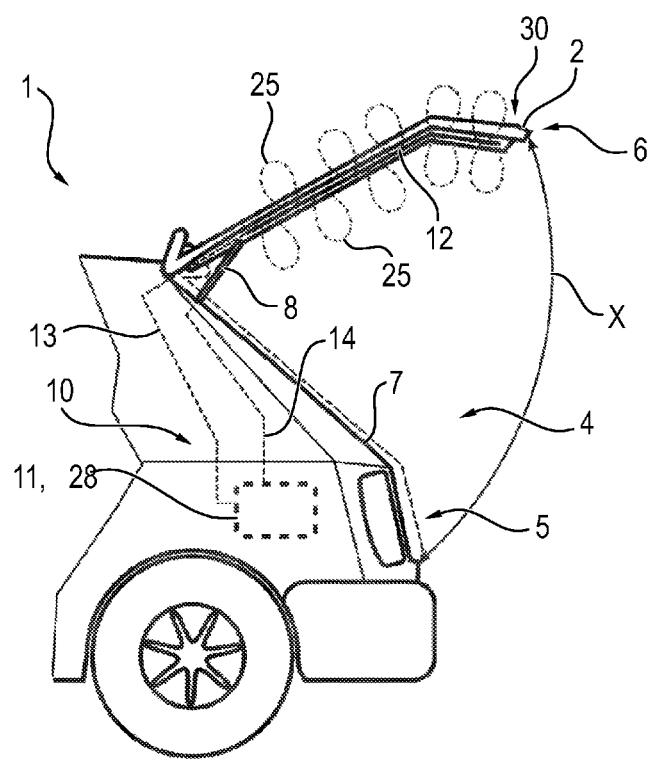
FIG. 1 is a diagrammatic, side view of a rear of a motor vehicle with a collision protection device and a capacitive proximity sensor associated with the same according to the invention.

Mutually corresponding parts are always provided with the same reference characters in all figures.

Referring now to the figures of the drawings in detail and first, particularly to FIG. 1 thereof, there is shown a rear of a motor vehicle 1 with a tailgate 2 disposed thereon is schematically represented in FIG. 1. The tailgate 2 is linked to the rear of the motor vehicle 1 so as to be pivotable about an upper edge. The tailgate 2 is a displaceable vehicle part that is disposed in the rear region for the reversible closure of a trunk opening 4. For this purpose, the tailgate 2 is pivotable along a travel distance X between a closed position 5 (indicated by a dashed line) and an open position 6. In the closed position 5 the tailgate 2 is in contact with a vehicle frame 7 of the motor vehicle 1 bounding the trunk opening 4 and thus closes the trunk opening 4.

The tailgate 2 is driven by an electric motor adjusting unit 8 for displacement between the closed position 5 and the open position 6. For this purpose, the adjusting unit 8 contains an electric motor and a gearbox disposed downstream of the electric motor in a manner that is not shown in detail, by which the adjusting force produced by the electric motor is transferred to the tailgate 2.

The motor vehicle 1 contains a collision protection device 10 in order to prevent an obstacle, for example a body part of a person or another object, from colliding with the moving tailgate 2 during displacement of the tailgate 2, i.e. during opening of the tailgate 2 from the closed position 5 into the open position 6 or when closing the tailgate 2 in the opposite direction. The collision protection device 10 contains a collision protection control unit (referred to in short below as a control unit 11) and a capacitive (proximity) sensor 12. In this case the capacitive sensor 12 is coupled to the control unit 11 for signal transmission by a sensor line 13.

The control unit 11 is configured to detect an obstacle in a region of control travel upstream of the tailgate 2 in the displacement direction during a displacement of the tailgate 2 while carrying out a collision protection method that is described below in detail, and possibly to stop or reverse the motor of the adjusting unit 8. For this purpose, the control unit 11 has a signal transmission connection to the adjusting unit 8 by a control line 14.

Figure 2:
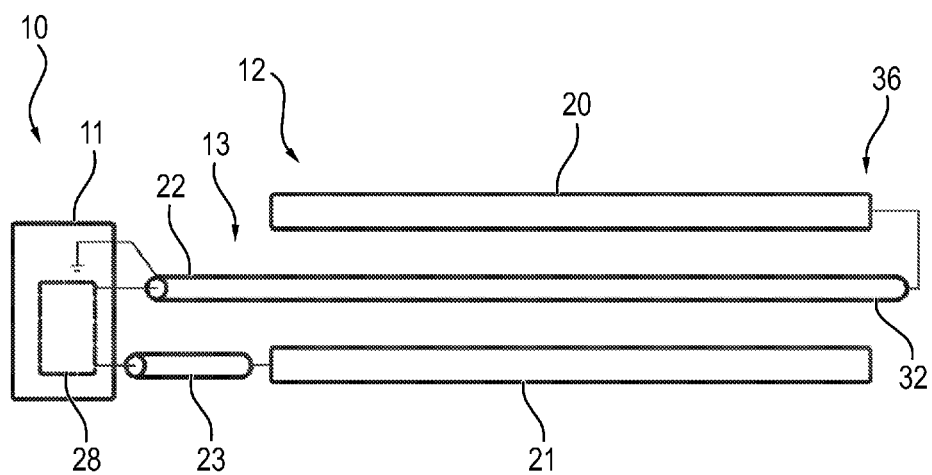
FIG. 2 is an illustration of the collision protection device with the proximity sensor.

The collision protection device 10 is shown schematically in detail in FIG. 2. The capacitive sensor 12 contains a first sensor electrode that is referred to as a transmission electrode 20 and a second sensor electrode that is referred to as a reception electrode 21 for the detection of an obstacle upstream of the tailgate 2 in the displacement direction. The sensor line 13 from the control unit 11 to the capacitive sensor 12 accordingly contains a shielded connecting line that is associated with the transmission electrode 20 and that is referred to below as a transmission line 22. Furthermore, the sensor line 13 contains a second shielded connecting line that is associated with the reception electrode 21 and that is referred to below as a reception line 23. The transmission line 22 and the reception line 23 are both implemented as coaxial cables, the respective inner conductors of which are used as dedicated conductors for the respective (electrical) signals. By applying an electrical (alternating) voltage, an electrical alternating field referred to as a measurement field 25 (i.e. an electrical field in which the field strength periodically changes sign) is built up between the transmission electrode 20 and the reception electrode 21 (indicated in FIG. 3 and FIG. 4 by dash-dotted field lines 26). As shown in FIG. 1, the measurement field 25 is built up on both sides (i.e. the inside and the outside) of the tailgate 2. This means that the measurement field 25 is radiated from the capacitive sensor 12 both in the opening direction and also in the closing direction. The transmission electrode 20 and the reception electrode 21 of the capacitive sensor 12 form an electrical capacitor in this case, the capacitance of which is detected by an analysis unit 28 of the capacitive sensor 12. In this case the analysis unit 28 is integrated within the control unit 11.

The control unit 11 is configured to draw conclusions regarding the approach of an object towards the tailgate 2 using a change in the capacitance of the sensor 12. If the change in the capacitance exceeds a predetermined reference value, the control unit 11 sends a control command to the adjusting unit 8 by the control line 14 to stop the adjustment movement.

It is recognized that the measurement field 25 is influenced both by (electrically) conducting and also non-conducting objects. Because the measurement field 25 is radiated both towards the outside and also towards the inside of the tailgate 2, in particular in the case in which there is liquid (for example rain water) on an external surface 30 of the tailgate 2 in the region of the capacitive sensor 12, such a large influence on the measurement field 25 and hence the capacitance of the sensor 12 can occur that the control unit 11 erroneously concludes that an obstacle is present in the range of travel of the tailgate 2 and hence stops the displacement of the tailgate 2.

In order to reduce the sensitivity of the capacitive sensor 12 to conducting or non-conducting objects that are disposed immediately at or on the outer surface 30 of the tailgate 2, and hence to increase the robustness of the detection of obstacles by the collision protection device 10, the sensor 12 contains a screen electrode. In this case the screen electrode is disposed between the transmission electrode 20 and the reception electrode 21. The screen electrode is specifically a cable shield 32 (the outer conductor of the coaxial cable) of the shielded transmission line 22 and is connected to reference potential (ground potential). As can be seen from FIG. 3, the cable shield 32 forms a sink for some of the field lines 26 emanating from the transmission electrode 20. Consequently, only those field lines 26 are received by the reception electrode 21 that run at a sufficiently long distance A, which is dependent on the geometry of the cable shield 32, from the cable shield 32 and hence also run to the outer surface 30 of the tailgate 2. This means that, owing to the cable shield 32 connected to ground potential between the transmission electrode 20 and the reception electrode 21, a region with reduced sensitivity is formed on the outer surface 30 of the tailgate 2 (also referred to below as a measurement field-free space)—i.e. the field lines 26 running from the transmission electrode 20 to the cable shield 32 do not contribute to the "active", i.e. detectable component of the measurement field 25.

As can be seen from FIG. 2, the transmission electrode 20 and the reception electrode 21 are each implemented in an elongated form. In this case the transmission line 22 and hence also the cable shield 32 are led along from the analysis unit 28 (or the control unit 11), between the transmission and reception electrodes 20 and 21 to the end 36 of the transmission electrode 20 that is remote from the analysis unit 28. As a result, a measurement field 25 is also of an almost constant shape over the entire length of the transmission and reception electrodes 20 and 21.

In order to be able to mount the transmission and reception electrodes 20 and 21 as well as the cable shield 32 on the motor vehicle 1, specifically on the tailgate 2, in a simple manner and in a predetermined spatial arrangement relative to each other, the capacitive sensor 12 contains a (sensor) base support 38. A plurality of holding elements 40 are disposed on the base support 38, by which the respective electrodes, i.e. the transmission electrode 20, the reception electrode 21 and the screen electrode (or the cable shield 32), are held in predetermined positions relative to each other (see FIG. 3 and FIG. 4). Here the holding elements 40 (only indicated schematically) are in the form of snap hooks for positive locking retention of the respective electrodes 20, 21, or 32. The base support 38 thus forms a premounted mounting assembly with the electrodes 20, 21, and the cable shield 32 mounted thereon, the assembly being fixed as such on the motor vehicle 1, specifically on the inside of the tailgate 2.

It can be seen in FIG. 3 that the shielded transmission line 22 and hence the cable shield 32 lie in a plane spanned by the transmission electrode 20 and the reception electrode 21 and referred to as a sensor plane E. As a result, a symmetrical formation of the measurement field 25 on both sides of the sensor plane E is achieved (i.e. a course of the field lines 26 that is axially symmetrical to the sensor plane E).

A further exemplary embodiment of the capacitive sensor 12 (or the collision protection device 10) is shown in FIG. 4. In this exemplary embodiment, the holding elements 40 of the base support 38 for the cable shield 32 are implemented with a different length (specifically shorter) compared to the holding elements for the transmission and reception electrodes 20 or 21. Thus the cable shield 32 is disposed offset to one side of the sensor plane E. This results in a course of the field lines 26 (schematically indicated in FIG. 4) that is asymmetrical relative to the sensor plane E. In the exemplary embodiment shown in FIG. 4, the measurement field-free space is enlarged in the region of the outer surface 30 of the tailgate 2 compared to the measurement field-free space on the inside (and compared to the exemplary embodiment according to FIG. 3).

In an exemplary embodiment that is not shown in detail, instead of the transmission line 22, the reception line 23 is fed between the transmission electrode 20 and the reception electrode 21, so that the corresponding cable screen thereof forms the screen electrode of the capacitive sensor 12. In a further exemplary embodiment that is not shown in detail, both the transmission line 22 and also the reception line 23 are led to the end 36 of the transmission electrode 20 and of the reception electrode 21 that is remote from the analysis unit 28.

Figure 5:
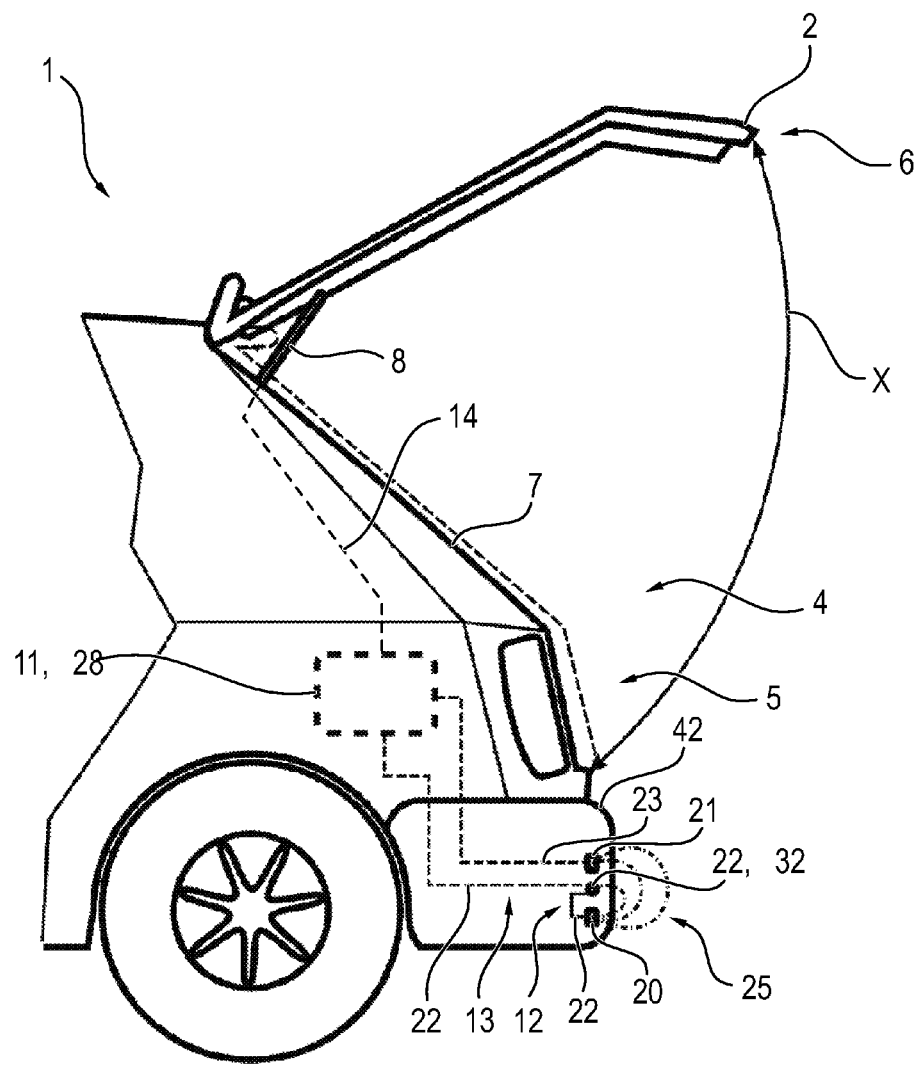
FIG. 5 is a side view of the rear of the motor vehicle showing an alternative use of the proximity sensor with the motor vehicle.

In a further exemplary embodiment according to FIG. 5, the control unit 11 is (in addition to or as an alternative to the collision protection device) in the form of part of a keyless access system for contactless detection of an intention to open a door. The capacitive sensor 12 (used for this purpose) is also used for the detection of a proximity event at the sensor 12. In this case the capacitive sensor 12 (oriented in the lateral direction of the vehicle) is disposed on the inside of a rear bumper 42 of the motor vehicle 1. If the vehicle user approaches the rear bumper 42, the measurement field 25 of the sensor 12 is influenced and the capacitance of the sensor 12 changes. The change in capacitance is detected in the control unit 11 and compared with a stored reference. In the event of sufficient agreement, the control unit 11 concludes that there is the intention to open a door on the part of the vehicle user and thereupon outputs a suitable control command to the motor of the adjusting unit 8 by the control line 14.

Owing to the arrangement of the screen electrode, i.e. of the grounded (connected to ground potential) cable shield 32 between the transmission electrode 20 and the reception electrode 21, the robustness of the capacitive sensor 12 against erroneous detections of a proximity event, in particular owing to rain water running off the surface of the rear bumper 42, is also increased with this exemplary embodiment.

The subject matter of the invention is not limited to the exemplary embodiments described above. Rather, further embodiments of the invention can be derived from the above description by the person skilled in the art. In particular, the individual features of the invention and the configurational variants thereof that were described using the various exemplary embodiments can also be combined in a different way.

The following is a summary list of reference numerals and the corresponding structure used in the above description of the invention:
1 motor vehicle
2 tailgate
4 trunk opening
5 closed position
6 open position
7 vehicle frame
8 adjusting unit
10 collision protection device
11 control unit
12 proximity sensor
13 sensor line
14 control line
20 transmission electrode
21 reception electrode
22 transmission line
23 reception line
25 measurement field
26 field line
28 analysis unit
30 outer surface
32 cable shield
36 end
38 base support
40 holding element
42 rear bumper
X range of travel
A distance
E sensor plane

The invention claimed is:

1. A capacitive proximity sensor for a motor vehicle, the capacitive proximity sensor comprising:
   a transmission electrode having an elongated shape for producing a measurement field;
   a reception electrode having an elongated shape for detecting at least part of the measurement field;
   a screen electrode disposed to form the measurement field between said transmission electrode and said reception electrode, said screen electrode is connected to a ground potential and is disposed spatially between said transmission electrode and said reception electrode for forming the measurement field over an entire length of said transmission and reception electrodes;

an analysis unit;

a first shielded connecting line connecting said analysis unit to said transmission electrode;

a second shielded connecting line connecting said analysis unit to said reception electrode; and said screen electrode is a cable shield of said first shielded connecting line or said second shielded connecting line.

2. The capacitive proximity sensor according to claim 1, further comprising:

predefined holding elements; and a base support, on said base support said transmission electrode, said reception electrode and said screen electrode are held by said predefined holding elements.

3. A collision protection device for a motor vehicle, the collision protection device comprising:

a capacitive proximity sensor containing a transmission electrode having an elongated shape for producing a measurement field, a reception electrode having an elongated shape for detecting at least part of the measurement field, and a screen electrode disposed to form the measurement field between said transmission electrode and said reception electrode, said screen electrode is connected to a ground potential, said screen electrode is disposed spatially between said transmission electrode and said reception electrode for forming the measurement field over an entire length of said transmission and reception electrodes;

a control unit configured to infer a presence of an object within a region upstream of a vehicle part that is monitored using the measurement field by using the part of the measurement field that is detected by said reception electrode;

a first shielded connecting line connecting said control unit to said transmission electrode;

a second shielded connecting line connecting said control unit to said reception electrode; and said screen electrode is a cable shield of said first shielded connecting line or said second shielded connecting line.

4. A motor vehicle, comprising:

a capacitive proximity sensor containing a transmission electrode having an elongated shape for producing a measurement field, a reception electrode having an elongated shape for detecting at least part of the measurement field, and a screen electrode disposed to form the measurement field between said transmission electrode and said reception electrode, said screen electrode is connected to a ground potential, said screen electrode is disposed spatially between said transmission electrode and said reception electrode for forming the measurement field over an entire length of said transmission and reception electrodes;

an analysis unit;

a first shielded connecting line connecting said analysis unit to said transmission electrode;

a second shielded connecting line connecting said analysis unit to said reception electrode; and said screen electrode is a cable shield of said first shielded connecting line or said second shielded connecting line.

* * * * *